(12) United States Patent
Gálik et al.

(10) Patent No.: US 8,450,476 B2
(45) Date of Patent: *May 28, 2013

(54) PROCESS FOR THE PREPARATION OF 17-HYDROXY-6β,7β;15β,16β-BISMETHYLENE-17α-PREGN-4-ENE-3-ONE-21-CARBOXYLIC ACID γ-LACTONE AND KEY INTERMEDIATES FOR THIS PROCESS

(75) Inventors: György Gálik, Albertirsa (HU); Judit Horváth, Budapest (HU); Béla Sörös, Budapest (HU); Sándor Mahö, Budapest (HU); Zoltán Tuba, Budapest (HU); Gábor Balogh, Budapest (HU)

(73) Assignee: Richter Gedeon Nyrt., Budapest (HU)

( * ) Notice: Subject to any disclaimer, the term of this patent is extended or adjusted under 35 U.S.C. 154(b) by 1179 days.

This patent is subject to a terminal disclaimer.

(21) Appl. No.: 11/719,463

(22) PCT Filed: Oct. 11, 2005

(86) PCT No.: PCT/HU2005/000111
§ 371 (c)(1),
(2), (4) Date: May 16, 2007

(87) PCT Pub. No.: WO2006/059168
PCT Pub. Date: Jun. 8, 2006

(65) Prior Publication Data
US 2008/0194812 A1    Aug. 14, 2008

(30) Foreign Application Priority Data
Nov. 30, 2004  (HU) ..................... 0402466

(51) Int. Cl.
*C07J 53/00*    (2006.01)

(52) U.S. Cl.
USPC .......................................... 540/15

(58) Field of Classification Search
USPC .......................................... 540/15
See application file for complete search history.

(56) References Cited

U.S. PATENT DOCUMENTS

| | | | |
|---|---|---|---|
| 3,470,160 A | 9/1969 | Schmidt et al. |
| 3,676,467 A | 7/1972 | Furst et al. |
| 4,129,564 A | 12/1978 | Wiechert et al. |
| 4,435,327 A | 3/1984 | Petzoldt et al. |
| 4,614,616 A | 9/1986 | Petzoldt et al. |
| 6,121,465 A | 9/2000 | Mohr et al. |
| 6,610,844 B2 | 8/2003 | Ng et al. |
| 2004/0024202 A1 | 2/2004 | Miller et al. |

OTHER PUBLICATIONS

K. Petzoldt et al., A Novel Synthetic Route to the Aldosterone-Antagonist Spirorenone, Angewandte Chemie International Edition, 1983, pp. 406-407, vol. 22, No. 5.
D. Bittler et al., Synthesis of Spirorenone—A Novel Highly Active AldoSterone Antagonist, Angewandte Chemie International Edition, 1982, pp. 696-697, vol. 21, No. 9.
P. Norman et al., Contraceptive Hormone Replacement Therapy Aldosterone Antagonist Progestogen, Drugs of the Future, Dec. 2000, pp. 1247-1256, vol. 25, No. 12, Spain.

*Primary Examiner* — Barbara P Badio
(74) *Attorney, Agent, or Firm* — Jason D. Voight

(57) ABSTRACT

The invention relates to a process for the preparation of 17-hydroxy-6β,7β;15β,16β-bismethylene-17α-pregn-4-ene-3-one-21-carboxylic acid γ-lactone of formula (I) as well as to key-intermediates for this process.

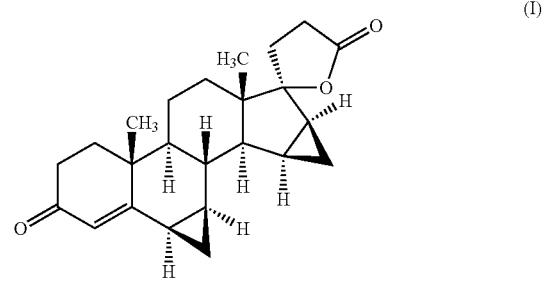

10 Claims, No Drawings

PROCESS FOR THE PREPARATION OF 17-HYDROXY-6β,7β;15β,16β-BISMETHYLENE-17α-PREGN-4-ENE-3-ONE-21-CARBOXYLIC ACID γ-LACTONE AND KEY INTERMEDIATES FOR THIS PROCESS

This is the National Stage of International Application PCT/HU2005/000111, filed Oct. 11, 2005.

The object of the invention is a process for the preparation of the known 17-hydroxy-6β,7β;15β,16β-bismethylene-3-oxo-17α-pregn-4-ene-21-carboxylic acid γ-lactone (hereinafter: drospirenone) of the formula (I),

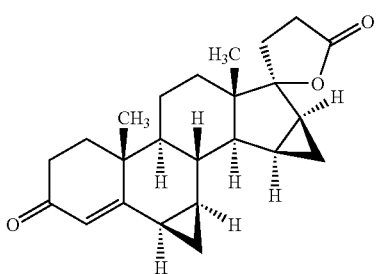

from 15α-hydroxy-androst-4-ene-3,17 dione of the formula (II).

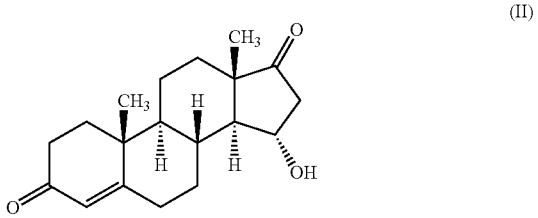

In the therapy the drospirenone is used as synthetic progestin having also anti-mineralocorticoid and antiandrogenic effects. In combination with ethynylestradiol it is marketed under the name of Yasmin as an oral contraceptive.

For the preparation of drospirenone of the formula (I) several processes are known in the chemical literature which differ in the starting material used and in the order of the reaction steps. Introduction of the functional groups is accomplished by known chemical methods.

A synthesis of drospirenone is first disclosed in the German patent specification DE 2,652,761. The synthesis starts from 3β-hydroxy-15β,16β-methyleneandrost-5-en-17-one which is reacted with 1-bromo-3,3-dimethoxypropane in tetrahydrofuran in the presence of lithium, followed by a cyclization in position 17 carried out in 70% acetic acid to give the "lactol-ether". The hydroxy and ether groups being present in the molecule were oxidized with cyclohexanone in the presence of aluminium isopropylate, then the double bond was izomerized by using 2N sulfuric acid to yield 17-hydroxy-15β,16β-methylene-3-oxo-17α-pregn-4-ene-21carboxylic acid γ-lactone.

The "γ-lactone" so obtained was reacted with chloranil (tetrachlorobenzoquinone) in t-butanol to form the "3-oxo-androsta-4,6-diene" in which a methylene group was introduced in positions 6,7 (by using trimethylsulfoxonium iodide and sodium hydride producing in situ a "methylide") giving the drospirenone.

For the preparation of 3β-hydroxy-15β,16β-methyleneandrost-5-ene-17-one (the starting material for the above synthesis) a five step reaction route is disclosed in the German patent specification DE 1,593,500.

The first synthesis for drospirenone was typically carried out by reactions difficult-to-perform and gave poor yields. Purification of the intermediates and the end-product accomplished by chromatography gave also low yields (49%, 26% and 16%, respectively).

In the German patent specification DE 2,746,298 intermediates which can be used also for the preparation of drospirenon are described. To form double bonds (which are required for the introduction of the methylene groups), first hydroxyl groups were brought into the molecule via a microbiological process. The dehydroepiandrosterone—the starting material for the synthesis—was hydroxylated microbiologically to give 3β,7α,15α-trihydroxyandrost-5-ene-17-one which, in turn, was oxidized in an additional fermentation step to yield 7α,15α-dihydroxyandrost-4-ene-3,17-dione. Elimination of the hydroxy group in position 15 was accomplished with p-toluenesulfonic acid catalyst yielding the "4,6,15-triene".

When the 7α,15α-dihydroxy derivative was acetylated with acetic anhydride in pyridine, 3β-acetoxy-7α-hydroxyandrost-5,15-diene-17-one was obtained in one step. The methylene group was introduced into positions 15,16 as discussed above and the compound obtained was oxidized microbiologically. Subsequent elimination of water gave the 15β,16β-methyleneandrosta-4,6-diene-3,17-dione. Then the compound having the "diene" structure in the AB rings of the steroid was treated with ethylene glycol in the presence of orthoformic acid trialkyl ester and p-toluenesulfonic acid catalyst to give the ketal in a manner known per se, said ketal was reacted with dimethoxybromopropane in the presence of lithium as described above to yield the "17-acetal", which then was cyclized to form the corresponding "lactol-methyl ether" and this was subjected to Jones oxidation to give the corresponding "lactone". The intermediate obtained in such a way has a double bond in position 6,7 to which a methylene group can be introduced in known manner.

Theoretically another synthesis route is described for the preparation of drospirenone in the European patent specification EP 051,143 and its equivalents (U.S. Pat. No. 4,416,985 and U.S. Pat. No. 4,614,616). The process is also published in Angew. Chem. 94, 718-719 (1982). What is novel is that the 6β,7β-methylene group is formed in a stereospecific manner by the Simmons-Smith reaction.

The starting material of the process is 3β-hydroxy-15β,16β-methyleneandrost-5-en-17-one. The hydroxy in 7β position is introduced in a fermentation process using *Botryodiplodia malorum*, the resultant compound is acetylated in a regioselective manner with pivalic anhydride in the presence of 4-dimethylaminopyridine yielding the corresponding 3β-pivaloyloxy derivative. Said pivaloyloxy derivative was reacted with tert-butyl hydroperoxide in the presence of VO (acetonylacetonate)₂ catalyst to give the 5β,6β-epoxy derivative which, in turn, was reacted with triphenylphosphine and carbon tetrachloride in dichloromethane to yield the 7α-chloro derivative. Said 7α-chloro derivative was reacted with zinc in a mixture of acetic acid and tetrahydrofuran yielding the 5β-hydroxy-15β,16β-methylene-3β-pivaloyloxyandrost-6-en-17-one which then was hydrolyzed with potassium hydroxide to give 3β,5β-dihydroxy-15β,16β-methyleneandrost-6-en-17-one.

Into the compound having a double bond in position 6 the methylene group was introduced by using diiodomethane in the presence of zinc in ethylene glycol dimethyl ether solvent and the "6β,7β;15β,16β-dimethylene" derivative so obtained was propynylated in position 17 in the presence of potassium ethylate in tetrahydrofuran. Said 17α-(3-hydroxy-1-propynyl)-6β,7β;15β,16β-dimethyleneandrostan-3β,5β,17β-triol was hydrogenated in a mixture of tetrahydrofuran, methanol and pyridine in the presence of Pd/CaCO$_3$ or Pd/C catalyst and the compound obtained was oxidized, lactonized and dehydrated in one step by using chromium trioxide in aqueous pyridine.

According to EP 0,051,143 instead of the pivaloyloxy protective group tert-butyldimethylsilyl, dimethyl-(3-methylbutyl)-silyl or tribenzylsilyl substituent are also suitable.

The synthesis consists of 15 steps. In the epoxidation step the use of the tert-butyl hydroperoxide is not without risk. When zinc dust is applied in a heterogeneous system under vigorous stirring a special apparatus is required. The sodium perchlorate is a hazardous material, the carbon tetrachloride as a reactant cannot already be used even at laboratory scale, whereas the potassium ethylate is flammable. Based on experiments, when an ethynyl group is hydrogenated, besides the completely hydrogenated product there are always partially hydrogenated impurities present and said impurities can only be separated with considerable loss of the useful compound either it is a straight chain or a cyclic one.

Both the EP 075,189 and the U.S. Pat. No. 4,435,327 patent specifications relate to combined synthetic/microbiological processes. Starting material for the synthesis is, again, the dehydroepiandrosterone which is dihydroxylated by a fermentation process (*Colletotrichum phomoides*) to give the 3β,7α,15α-trihydroxyandrost-5-en-17-one; the hydroxy substituent in position 7 of said compound is then epimerized by using 35% perchloric acid as catalyst e.g. in a mixture of acetone and dichloro-methane; finally the 3β,7β,15α-trihydroxy derivative is reacted with pivaloyl chloride in pyridine, in the presence of 4-dimethylaminopyridine catalyst to give the 3,15-pivaloylated derivate. An alternative process for the preparation of the compound is also disclosed.

The subsequent steps of the synthesis are the same as those described in EP 051,143.

Beyond that the process can be accomplished via 12 steps, it also uses the reactions mentioned before which require reactants and reaction conditions that are not without danger.

In the German patent specification DE 3,626,832 a different novel method for forming the γ-lactone ring is disclosed. The synthesis starts from 15β,16β-methylene-3-methoxy-androsta-3,5-diene-17-one which is reacted with 2-(1-ethoxyethoxy)-3-butenenitrile and the "unsaturated nitrile" derivative obtained is cyclized to form the γ-lactone structure in two steps. Difficulties of this process arise from the synthesis of a special reagent and the bromination in position 6.

According to the German patent specification DE 1,963,3683 (=U.S. Pat. No. 6,121,465) from known intermediates, i.e. from 17α(3-hydroxy-1-propynyl)-6β,7β;15β;16β-bismethyleneandrostan-3β,5β,17β-triol and 6β,7β;15β,16β-bismethylene-5β,17β-dihydroxy-3-oxo-17α-pregnane-21-carboxylic acid γ-lactone the drospirenone is prepared by a new process. The 17α-(3-hydroxy-1-propynyl)-6β,7β;15β,16β-bismethyleneandrostane-3β,5β,17β-triol is hydrogenated in tetrahydrofuran in the presence of palladium/carbon; the "bismethylenepropanol" obtained was suspended in acetonitrile, the suspension is heated to 45° C., then 1 mol % of ruthenium trichloride is added in aqueous solution. Subsequently aqueous solution of sodium bromate is added dropwise, the reaction mixture is kept at 50° C. for 2 hours then worked up by extraction method. The 6β,7β;15β,16β-bismethylene-5β,17β-dihydroxy-3-oxo-17α-pregnane-21-carboxylic acid γ-lactone obtained is recrystallized, dehydrated with p-toluenesulfonic acid and purified by chromatography. According to the specification the hydrogenation and oxidation step can be performed with 65-72% yield. The greatest advantage of this process is that no toxic chromium compound is used. In the previous steps of the process, however, there are several details which—as it is mentioned above—make difficult to meet safety requirements and make uncertain a possible scale-up of the process.

In the European patent EP 0,150,702 a process starting from androst-4-ene-3,17-dione is disclosed. The 15α-hydroxy derivative is prepared by a fermentation step, said compound is benzoylated to give an oily product which is reacted with trimethylsulfonium methylide prepared in situ from trimethylsulfonium iodide. From 40 g of 15α-hydroxyandrost-4-ene-3,17-dione after purification by chromatography 22.7 g of 15β,16β-methyleneandrost-4-ene-3,17-dione were obtained. The propargylation is carried out by reacting the compound with propargyl alcohol in the presence of potassium ethylate. A compound mixture is obtained in which the double bond of 17β-hydroxy-17β-(3-hydroxy-1-propynyl)-15β,16β-methylene-androst-5-ene-3-one component is izomerized into the "3-oxo-androst-4-ene" in an additional reaction step. Said "propynyl" derivative is hydrogenated in the presence of tris(triphenylphosphine)rhodium (I) chloride catalyst, formation of the lactone ring is carried out by using chromium trioxide in pyridine. The "γ-lactone" obtained is reacted with orthoformic acid triethyl ester to yield 3-ethoxy-17-hydroxy-15β,16β-methylene-17α-pregna-3,5-diene-21-carboxylic acid γ-lactone which at position 6 is brominated, the oily product obtained is reacted with lithium bromide and lithium carbonate in dimethylformamide at 100° C. to give the 17-hydroxy-15β,16β-methylene-3-oxo-17α-pregna-4,6-diene-21-carboxylic acid γ-lactone intermediate after purification by chromatography. Difficulties arising from hydrogenation of propynyl compound and from the bromination at position 6 were discussed above.

According to the German patent specification DE 1,920,145 3-methoxy-15β,16β-methyleneandrosta-3,5-diene-17-one is synthesized from 15β,16β-methyleneandrosta-4-ene-17-one, which is refluxed with catalytic amount of p-toluenesulfonic acid and 2,2-dimethoxypropane in the presence of methanol in dimethylformamide. Said "3-methoxy" derivative can be used as intermediate for the preparation of drospirenone.

According to recent pharmacopoieal requirements several tests (e.g. TLC or HPLC) are specified to control purity of the drugs which may contain only a limited number of impurities in limited amount. To meet these requirements it is practical to know what impurities and in which amount are present in the intermediates. For this purpose analytical control of the intermediates at adequate level is necessary to obtain drugs at plant scale in good quality and to determine which purification steps are necessary or which process stops can be combined to make the process profitable.

Taking into consideration the above aspects our aim is to provide a process suitable for industrial use, which is safe and lacks the drawbacks of the previous processes and by which the drug obtained is pure and meets all the pharmacopoieal requirements. Enclosed is a flow sheet 1/1 showing the whole synthesis route in an easy-to-follow form (numbered as 1/2 and 2/2 pages).

We have surprisingly found that all requirements can be met by the process as follows:

15α-hydroxy-androst-4-ene-3,17-dione of the formula (II),

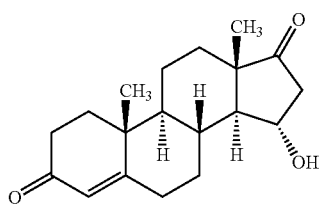

(II)

is acetylated with acetic anhydride in dry tetrahydrofuran in the presence of 4-dimethylaminopyridine catalyst at room temperature to give the 15α-acetoxyandrost-4-ene-13,17-dione of the formula (III),

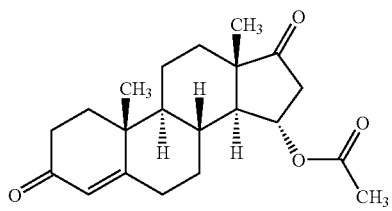

(III)

said compound of the formula (III) in dry tetrahydrofuran is reacted with a trialkoxy orthoformate containing alkyl groups having from 1 to 5 carbon atoms, in the presence of sulfuric acid catalyst at 0-10° C. temperature to yield 15α-acetoxy-3-alkoxy-androsta-3,5-diene-17-one of the general formula (IV),

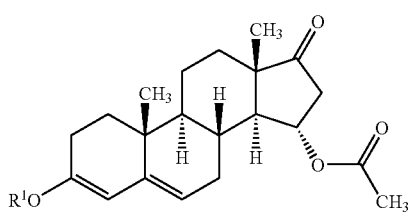

(IV)

wherein $R^1$ stands for an alkyl group having 1-4 carbon atoms, said compound of the general formula (IV) is reacted with a trimethylsulfoxonium methylide in situ prepared in dimethyl sulfoxide from a trimethylsulfoxonium salt with an alkali metal hydroxide, to give the 15β,16β-methylene-3-alkoxy-androsta-3,5-diene-17-one of the general formula (V),

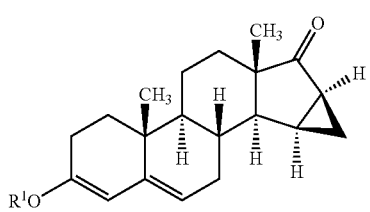

(V)

said compound of the general formula (V)—wherein $R^1$ stands for an alkyl group having 1-4 carbon atoms—in dimethyl sulfoxide is reacted with trimethysulfonium iodide in the presence of potassium tert-butylate at a temperature of 15-25° C. to give the 15β,16β-methylene-3-alkoxy-spiro[androsta-3,5-diene-17β2'-oxirane] of the general formula (VI),

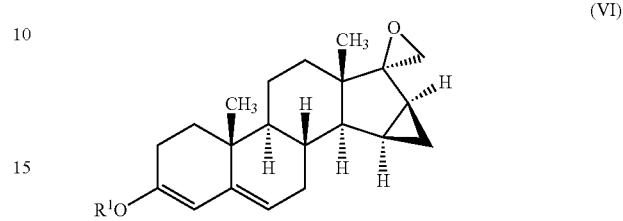

(VI)

wherein $R^1$ stands for an alkyl group having 1-4 carbon atoms, said compound of the of the formula (VI) in ethanol is reacted with a di($C_{1-4}$ alkyl) malonate in the presence of sodium ethoxide under boiling to yield 17-hydroxy-15β,16β-methylene-3-alkoxy-17α-pregna-3,5-diene-21,21-dicarboxylic acid alkyl ester γ-lactone of the general formula (VII),

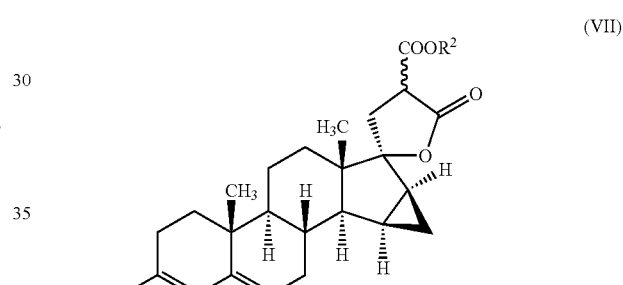

(VII)

wherein $R^1$ and $R^2$ stand for an alkyl group having 1-4 carbon atoms, and the ~ bond represents α and β configuration, said compound of the general formula (VII) is dehydrogenated with tetrachlorobenzoquinone in acetone to give 17-hydroxy-15β,16β-methylene-3-oxo-17α-pregna-4,6-diene-21,21-dicarboxylic acid alkyl ester γ-lactone of the general formula (VIII),

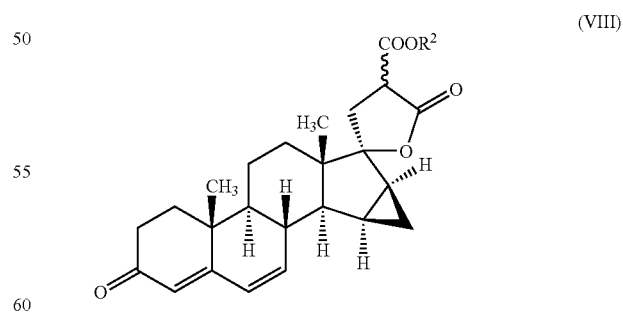

(VIII)

wherein $R^2$ stands for an alkyl group having 1-4 carbon atoms and the ~ bond represents α and β configuration, said compound of the general formula is reacted with trimethylsulfoxonium methylide in situ prepared in dimethyl sulfoxide from a trimethylsulfoxonium salt and an alkali metal hydroxide to give 17-hydroxy-6ξ,7ξ;15β,16β-bismethylene-3-oxo-17α-pregn-4-ene-21,21-dicarboxylic acid alkyl-ester γ-lactone of the general formula (IX),

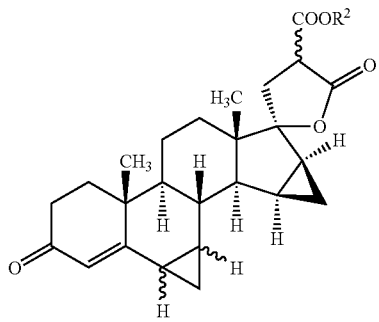

(IX)

wherein $R^2$ is an alkyl group having 1-4 carbon atoms and the ~ bond represents α and β configuration,
and either from said compound of the general formula (IX) the 17-hydroxy-6β,7β;15β,16β-bismethylene-3-oxo-17α-pregn-4-ene-21,21-dicarboxylic acid alkyl ester γ-lactone (an isomer of the general formula (IXa)) is isolated by chromatography and recrystallization—in formula (IXa) $R^2$ and the ~ bond are as defined above—

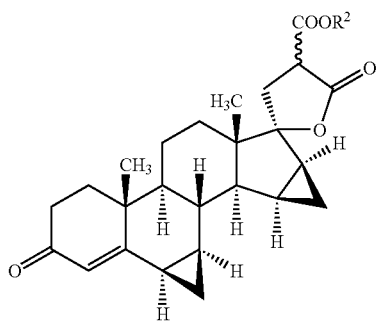

(IXa)

and said isomer of the general formula (IXa) in dimethylformamide is decarboxylated at a temperature around the boiling point of the reaction mixture to give the 17-hydroxy-6β,7β;15β,16β-bismethylene-3-oxo-17α-pregn-4-ene-21-carboxylic acid γ-lactone of the formula (I) which is isolated,
or the 17-hydroxy-6ξ,7ξ;15β,16β-bismethylene-3-oxo-17α-pregn-4-ene-21,21-dicarboxylic acid alkylester γ-lactone of the general formula (IX),

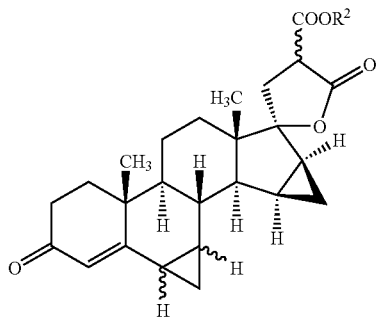

(IX)

wherein $R^7$ stands for an alkyl group having 1-4 carbon atoms and the ~ bond represents α and β configuration— in dimethylformamide is decarboxylated at temperature around the boiling point of the reaction mixture to give 17-hydroxy-6ξ,7ξ;15β,16β-bismethylene-3-oxo-17α-pregn-4-ene-21-carboxylic acid γ-lactone of the formula (X),

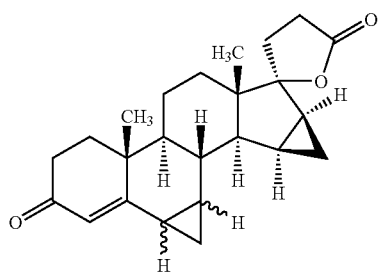

(X)

wherein the ~ bond represents α and β configuration,— from which the 17-hydroxy-6β,7β;15β,16β-bismethylene-3-oxo-17α-pregn-4-ene-21-carboxylic acid γ-lactone of the formula (I) is separated by chromatography and recrystallization; or
the 17-hydroxy-15β,16β-methylene-3-oxo-17α-pregna-4,6-diene-21,21-dicarboxylic acid allyl ester γ-lactone of the general formula (VIII)

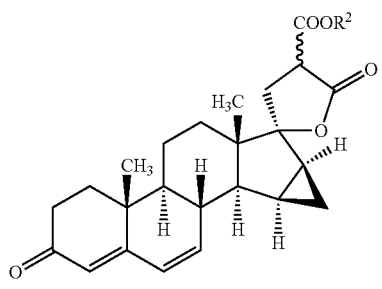

(VIII)

wherein $R^2$ stands for an alkyl group having 1-4 carbon atoms and the ~ bond represents α and β configuration—in dimethylformamide is decarboxylated at a temperature around the boiling point of the reaction mixture, to give the 17-hydroxy-15β,16β-methylene-3-oxo-17α-pregna-4,6-diene-21-carboxylic acid γ-lactone of the formula (VIIIa) which is isolated,

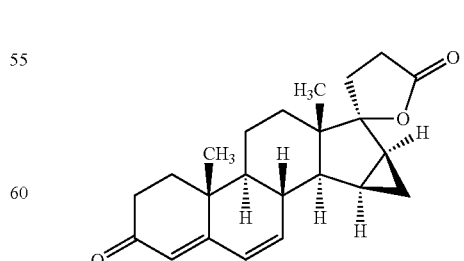

(VIIIa)

said compound of the formula (VIIIa) is reacted with trimethylsulfoxonium methylide prepared in situ in dimethyl sulfoxide from a trimethylsulfoxonium salt and an alkali metal hydroxide to yield 17-hydroxy-6ξ,7ξ;15β,16β-bismethylene-3-oxo-17α-pregn-4-ene-21-carboxylic acid γ-lactone of the formula (X),

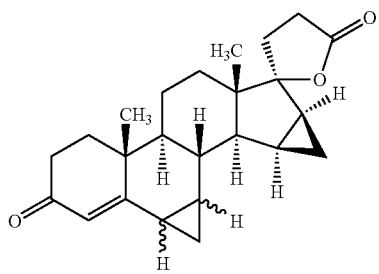

wherein the ~ bond represents α and β configuration,—and from said compound of the formula (X) the 17-hydroxy-6β,7β;15β,16β-bismethylene-3-oxo-17α-pregn-4-ene-21-carboxylic acid γ-lactone of the formula (I) is separated by chromatography and recrystallization.

According to this invention the 15α-hydroxy-androst-4-ene-3,17-dione of the formula (II) (Chem. Ind. 1956, 111) preferably is reacted with acetic anhydride in dry tetrahydrofuran in the presence of 4-dimethylaminopyridine below a temperature of 40° C., after the reaction has been completed the reaction mixture is added to water, when the precipitate is dense enough it is filtered, washed until it is free of mother liquor and dried. The 15α-acetoxyandrost-4-ene-3,7-dione of the formula (III) is obtained with 88% yield in a process which is easy to carry out and easy to scale up to any reasonable size. The compound obtained can be used in the next reaction step without further purification.

The 15α-acetoxy-androst-4-ene-3,17-dione of the formula (III) is then dissolved in dry tetrahydrofuran, the solution is cooled to 0° C. and in the presence of sulfuric acid catalyst is reacted preferably with trimethyl or triethyl orthoformate. When the reaction is complete, to the solution pyridine is added and the tetrahydrofuran is distilled off using a solvent replacement technique (THF is changed to acetonitrile). The crystalline product is filtered and dried. The 15α-acetoxy-3-alkoxy-androsta-3,5-diene-17-one—wherein $R^1$ is a methyl or ethyl group—(general formula (IV)) is obtained with 95% yield.

The 15α-acetoxy-3-alkoxy-androsta-3,5-diene-17-one of the general formula (IV) is treated with a reagent prepared in situ from trimethylsulfoxonium iodide and potassium hydroxide in a solvent, the reaction mixture is stirred for 6 hours then added to water. The precipitate is filtered off, washed to remove the mother liquor and dried.

The 15β,16β-methylene-3-alkoxy-androsta-3,5-diene-17-one obtained (general formula (V)), wherein R stands for methyl or ethyl group) is dissolved in dry dimethyl sulfoxide and in nitrogen atmosphere is reacted with trimethylsulfonium iodide and potassium tert-butylate at 18-22° C. After about 1.5 hour reaction time the solution is added to water, the precipitate formed is filtered, washed to remove the mother liquor, dried and purified by stirring in methanol.

The 15β,16β-methylene-3-alkoxy-spiro[androsta-3,5-diene-17β,2'-oxirane] obtained (general formula (VI)), wherein $R^1$ stands for a methyl or ethyl group) is the added in nitrogen atmosphere to a solution containing sodium ethylate in situ prepared from sodium and ethanol, as well as diethyl or dimethyl malonate (said solution was previously refluxed for 30 minutes) and reacted for 6 hours at 55-60° C. The solution is then cooled to room temperature, neutralized with acetic acid and diluted with water. The precipitate formed is washed until neutral, then dried.

The 17-hydroxy-15β,16β-methylene-3-alkoxy-17α-pregna-3,5-diene-21,21-dicarboxylic acid alkyl ester γ-lactone (a compound of general formula (VII), wherein $R^1$ and $R^2$ stand for methyl or ethyl group) obtained in the previous step is reacted with tetrachlorobenzoquinone in aqueous acetone under vigorous stirring in nitrogen atmosphere at room temperature. After the reaction has been completed the excess of benzoquinone is decomposed with aqueous sodium pyrosulfite solution, and from the aqueous solution the acetone is removed in vacuo. The target compound is extracted with dichloromethane, the organic layer is washed and dried, then the solvent is evaporated. To the residue methanol is added which, again, is evaporated and the remaining product is isolated by filtration yielding 17-hydroxy-15β,16β-methylene-3-oxo-17α-pregna-4,6-diene-21,21-dicarboxylic acid alkyl ester 7γ-lactone of the general formula (VIII), wherein $R^2$ stands for methyl or ethyl group.

The obtained "lactone" of the general formula (VIII) in nitrogen atmosphere is reacted with trimethylsulfoxonium methylide prepared in situ in dimethyl sulfoxide from trimethylsulfoxonium iodide and potassium hydroxide. The reaction mixture is stirred for 24 hours at room temperature, then added to water containing hydrochloric acid. The precipitate formed is filtered, washed until is neutral and dried at room temperature.

The 17-hydroxy-6ξ,7ξ;15β,16β-bismethylene-3-oxo-17α-pregn-4-ene-21,21-dicarboxylic acid alkyl-ester γ-lactone mixture of the formula (IX) is purified by a preliminary and a fine chromatographic step (e.g. as described in Example 8) using silica gel column and the obtained compound of the general formula (IXa) carrying the β-methylene group already in β configuration in position 6,7 is decarboxylated to give the drospirenone.

In another embodiment of the invention first the isomeric mixture of the general formula (IX) is decarboxylated to give the "6α,7α and 6β,7β" methylene isomeric mixture of the general formula (X) which is subjected to chromatography.

Decarboxylation of the isomeric mixtures either of the general formula (IX) or (IXa) is carried out in the same way: the mixtures are refluxed in dimethylformamide containing sodium chloride and some water for 8 hours in nitrogen atmosphere. The solution is then cooled to room temperature, diluted with water and the precipitated product is extracted with dichloromethane. From the extract the dichloromethane is removed by distillation at atmospheric pressure, whereas the dimethylformamide is distilled off at 13.3 Pa (0.1 mmHg). The residue is triturated in water, filtered, washed to remove the mother liquor and dried.

The obtained 17-hydroxy-6ξ,7ξ;15β,16β-bismethylene-3-oxo-17α-pregn-4-ene-21-carboxylic acid γ-lactone of the formula (X) is subjected to column chromatography using Kieselgel Si60 (0.040-0.063 mm; Merck) and 1:1 mixture of ethyl acetate/cyclohexane. Fractions of the same composition are combined, the solvent is evaporated and to the residue cyclohexane is added. The precipitate is filtered and dried in vacuo. The column is regenerated with acetone, then conditioned with a cyclohexane/acetone mixture (ratio 73:27), and by using the mixture of the same ratio the pre-chromatographed product is subjected again to chromatography by repeated addition of 2 g portions at 90 min intervals. Fractions of the same composition are combined, the solvent is removed by distillation and the residue is crystallized from a dichloromethane/diisopropyl ether mixture of 10:90 ratio (v/v).

In another embodiment 17-hydroxy-15β,16β-methylene-3-oxo-17α-pregna-4,6-diene-21,21-dicarboxylic acid alkyl ester γ-lactone of the general formula (VIII) is decarboxylated. Said compound is refluxed in dimethylformamide containing sodium chloride and some water for 8 hours in nitrogen atmosphere. The solution is then cooled to room temperature, diluted with water and the precipitated product is extracted with dichloromethane. From the extract the dichloromethane is removed by distillation at atmospheric pressure, whereas the dimethylformamide is distilled off at 13.3 Pa (0.1 mmHg). The residue is triturated in water, filtered, washed to remove the mother liquor and dried. 17-hydroxy-15α,16β-methylene-3-oxo-17α-pregna-4,6-diene-21-carboxylic acid γ-lacton of the formula (VIIIa) is obtained which is reacted with trimethylsulfoxonium methylide prepared in situ to give 17-hydroxy-6ξ,7ξ;15β,16β-bismethylene-3-oxo-17α-pregn-4-ene-21-carboxylic acid γ-lactone of the formula (X), from which the compound of the formula (I) is prepared as described above.

The inventive step of this invention is supported by the following features:
a) The starting material of the synthesis (15α-hydroxy-androst-4-ene-3,17-dione) can easily be prepared from androst-4-ene-3,17-dione by a fermentation process.
b) Our process consists of 8 steps, while the other processes known in the art consist of 15, 12 and 10 steps, respectively,
c) According to this inventions intermediates are obtained with very good yields. In Example 1; the yield is 88%, in Example 2; 95%, in Example 3; 76%, in Example 4; 95.7%, Example 5; 83.1%, in Example 6; 77.2% in Example 7; 94.6%, and in Example 9; 79.8%. Processes known in the art have much lower yields.
d) Contrary to the processes known in the art in our process we neither use reagents already prohibited (e.g. carbon tetrachloride) nor other hazardous materials (e.g. tert-butyl hydroperoxide, sodium ethylate, sodium hydride, butyl lithium and sodium perchlorate). No special apparatus is required in our process, while those using e.g. zinc, need a special stirrer for the reaction carried out in heterogenous system.
e) Intermediates obtained in our process are easy to purify or can be used in the next reaction step without purification.
f) Intermediates that are strategically important in our process, are novel. Such new compound are of the general formula (VI), (VII), (VIII), (IX) and (IXa).
g) Even in the case of preparation of known intermediates we made efforts to use simpler methods than those known in the chemical literature and to achieve better yields. E.g. the 15-α-acetoxy-androst-4-ene-3,17-dione is prepared in a well reproducible way which is easy to scale-up with a yield of 88%, while in the literature a yield of 62% is given.
h) In the last synthetic step the product mixture is separated by combined pre- and fine chromatography with 45% yield which is an excellent result compared with the 16% given in the German patent specification DE 2,652,751.

The invention is illustrated with the following non-limiting Examples.

EXAMPLE 1

5α-Acetoxy-androst-4-ene-3,7-dione 84.5 of 15α-hydroxy-androst-4-ene-3,17-dione is suspended in 270 ml of dry tetrahydrofuran under nitrogen atmosphere with vigorous stirring at room temperature, then 0.50 g of 4-dimethylaminopyridine is added. To lids suspension 42.25 ml of acetic anhydride is added while the temperature is kept below 40°. During the reaction the mixture becomes clear. After addition of the acetic anhydride the reaction mixture is stirred for 30 minutes, then added slowly to 2700 ml of water and stirred for additional 2 hours until the precipitate formed becomes dense. The precipitate is filtered, washed with portions of water until it is neutral and dried to constant weight. The title compound so obtained can be used in the next reaction step without further purification.

Yield: 84.5 g (88%)
Mp: 149-151° C.
$[\alpha]_D^{25}=+176°$ (c=1%, ethanol).
$^1$H NMR {500 MHz, CDCl$_3$(TMS), δ (ppm)}: 1.00 (3H, s, 18-Me); 1.05 (1H, m, H-9); 1.22 (3H, d, 19-Me); 1.61 (1H, t, H-14); 1.94 (1H, m, H-8); 2.02 & 3.17 (2H, dd & dd, H-16); 2.05 (3H, s, O—CO—CH$_3$); 5.24 (1H, m, H-15); 5.75 (1H, m, H-4).
$^{13}$C NMR {125 MHz, CDCl3 (TMS), δ (ppm)}: 15.2 (C-18); 17.5 (C-19); 21.2 (—O—CO—CH$_3$); 35.2 (C-8); 43.4 (C-16); 53.6 (C-9); 53.8 (C-14); 71.6 (C-15); 124.1 (C-4); 169.6 (C-5); 170.7 (—O—CO—CH$_3$); 199.0 (C-3); 214.3 (C-17).

EXAMPLE 2

15α-Acetoxy-3-methoxy-androst-3,5-diene-17-one 84.5 g of 5α-acetoxy-androst-4-ene-3,7-dione is dissolved in 500 ml of dry tetrahydrofuran under nitrogen atmosphere with stirring. The solution is coded to 0° C. and 40 ml of trimethyl orthoformate and 8.5 ml of tetrahydrofurane containing 1 vol % of sulfuric acid are added in sequence. The reaction mixture is stirred for 5 hours at 0-2° C., at this time 27 ml of pyridine is added and stirring is continued for additional 20 minutes. The tetrahydrofuran is removed by distillation and continuously replaced by acetonitrile until one third of the original volume is obtained. The remaining acetonitrile contains a crystal suspension which is cooled to 0° C., filtered off, washed with acetonitrile cooled to 0° C. to remove the mother liquor and dried in vacuo to constant weight at 40° C. yielding 83.5 g (95%) of the title compound.

Mp. 206-211° C.,
$[\alpha]_D^{25}=-14°$ (c=1%, dioxane).
$[\alpha]_D^{25}=-13.5°$ (c=0.5%, chloroform).
$^1$H NMR {500 MHz, CDCl$_3$(TMS), δ (ppm)}: 0.99 (3H, s, 18-Me); 1.00 (1H, m, H-9); 1.13 (1H, m, H-9); 1.66 (1H, t, H-14); 2.02 & 3.14 (2H, dd & dd, H-16); 2.05 (1H, m, H-8); 2.07 (3H, s, —O—CO—CH$_3$); 3.58 (3H, s, —O—CH$_3$); 5.13 (1H, m, H-4); 5.20 (1H, m, H-6); 5.26 (1H, m, H-15).
$^{13}$C NMR {125 MHz, CDCl$_3$(TMS), δ (ppm)}: 15.0 (C-18); 19.0 (C-19); 21.2 (—O—CO—CH$_3$); 31.6 (C-8); 43.4 (C-16); 48.0 (C-9); 54.3 (—O—CH$_3$); 54.4 (C-14); 72.2 (C-15); 98.3 (C-4); 117.4 (C-6); 140.5 (C-5); 155.4 (C-3); 170.8 (—O—CO—CH$_3$); 214.9 (C-17).

EXAMPLE 3

15β,16β-methylene-3-methoxyandrosta-3,5-diene-17-one 64.8 g of trimethylsulfoxonium iodide is dissolved in 900 ml of dimethyl sulfoxide under nitrogen atmosphere with stirring and to this solution 27.55 g of potassium hydroxide is added at 25-30° C. The reaction mixture is stirred for 1 hour, then 81.1 g of 15α-acetoxy-3-methoxy-androst-3,5-diene- 17-one is added and stirring is continued at 25-30° C. until the reaction is finished (about additional 6 hours). The solution is slowly added to 4500 ml of water, the precipitate is compacted by stirring (30 minutes), filtered, washed with water until it is neutral and dried in vacuo to constant weight below 40° C. The title compound is crystallized from methanol.

Yield: 53.8 g (76%)
Mp: 159-161° C.
$[\alpha]_D^{25}=-177.6°$ (c=1%, dioxane).
$^1$H NMR {500 MHz, CDCl$_3$(TMS), δ (ppm)}: 1.00 (6H, s, 18-Me & 19-Me); 1.12 & 1.64 (2H, m & m, CP (15β,16β)(CH$_2$)); 1.15 (1H, m, H-9); 1.74 (1H, m, H-16); 1.97 (1H, m, H-15); 1.98 (1H, m, H-8); 2.00 (1H, m, H-14); 3.58 (3H, m, —O—CH$_3$); 5.16 (1H, d, H-4); 5.29 (1H, m, H-6).
$^{13}$C NMR {125 MHz, CDCl$_3$(TMS), δ (ppm)}: 17.1 (CP (15β,16β)(CH$_2$)); 18:9 (C-19); 20.1 (C-18); 22.1 (C-15); 25.8 (C-16); 30.4 (C-8); 49.3 (C-9); 52.4 (C-14); 54.3 (—O—CH$_3$); 98.4 (C-4); 117.3 (C-6); 141.5 (C-5); 155.5 (C-3); 216.5 (C-17).

EXAMPLE 4

15β,16β-Methylene-3-methoxy-spiro[androsta-3,5-diene-17β2'-oxirane]

50 g (0.16 mol) of 15β,16β-methylene-3-methoxyandrosta-3,5-diene-17-one is dissolved in 500 ml of dry dimethyl sulfoxide under nitrogen atmosphere with stirring, the solution is cooled to 18-22° C., 71.4 g (0.35 mol) of trimethylsulfonium iodide is added, then 50 g (0.446 mol) of potassium tert-butilate is added in portions, while temperature is kept at the same level. The mixture is stirred for 1.5 hour, added slowly to 5l of water, the precipitate formed is filtered, washed 3 times with 200 ml of water until neutral and dried in vacuo to constant weight below 40° C. yielding 51.86 g of the crude product which is purified in 260 ml methanol with stirring.

Yield: 50.0 g (95.71%)
Mp: 163-165° C.
$[\alpha]_D^{25}=-149.18°$ (C=1%, chloroform).
$^1$H NMR {500 MHz, CDCl$_3$(TMS), δ (ppm)}: 0.48 & 1,25 (2H, m & m, CP (15β,16β)(CH$_2$)); 0.96 (3H, s, 18-Me); 0.99 (3H, s, 19-Me); 1.04 (1H, m, H-16); 1.10 (1H, m, H-9); 1.47 (1H, m, H-15); 1.89 (2H, m, H-8 & H-14); 2.84 & 2.95 (2H, d & d, oxiran (CH$_2$)); 3.58 (3H, m, —O—CH$_3$); 5,16 (1H, m, H-4); 5.29 (1H, m, H-6).
$^{13}$C NMR {125 MHz, CDCl$_3$(TMS), δ (ppm)}: 9.6 (CP (15β,16β)(CH$_2$)); 17.2 (C-15); 18.7 (C-16); 18.9 (C-19); 20.4 (C-18); 30.9 (C-8); 49.1 (C-9); 53.1 (oxiran (CH$_2$)); 54.3 (—O—CH$_3$); 54.6 (C-14); 71.6 (C-17); 98.5 (C-4); 117.9 (C-6); 141.3 (C-5); 155.4 (C-3).

EXAMPLE 5

17-Hydroxy-15β,16β-methylene-3-methoxy-17α-pregna-3,5-diene-21,21-dicarboxylic acid ethyl ester γ-lactone 2.3 g (0.1 mol) of sodium chips are added to 230 ml of ethanol under nitrogen atmosphere with vigorous stirring about over 40 minutes. To this sodium ethylate solution prepared in situ, 23 ml (0.152 mol) of diethyl malonate is added, the solution is refluxed for 30 minutes, then temperature is reduced to 55-60° C. and 23 g (70.45 mmol) of 15β,16β-methylene-3-methoxy-spiro[androsta-3,5-diene-17β2'-oxirane] is added and the mixture is refluxed for 8 hours until the reaction has been completed. The solution is cooled to room temperature, pH is adjusted to 7 with 6 ml of acetic acid (0.105 mol), 100 ml of water is added, the fine precipitate formed is filtered and washed with water until neutral. The wet precipitate is purified by stag in 150 ml of methanol, washed twice with 20 ml of methanol cooled to 0° C. to remove the mother liquor, filtered and dried in vacuo to constant weight at a temperature below 40° C., yielding 25.8 g (83.12%) of the title compound.

Mp: 15-155° C.
$[\alpha]_D^{25}=-109.7°$ (c=0.5%, pyridine)
The product contains two isomers in about 2:1 molar ratio.
$^1$H NMR {500 MHz, CDCl$_3$(TMS), δ (ppm) [major/minor]}: 0.48 & 1.26/0.45 & 1.24 (2H, m & m, CP (15β,16β)(CH$_2$)); 0.991/1.01 (3H, s, 19-Me); 0.994/1.06 (3H, s, 18-Me); 1.08 (1H, m, H-9); 1.321/1.322 (3H, t, —O—CH$_2$—CH$_3$); 1.34/1.33 (1H, m, H-16); 1.43/1.41 (1H, m, H-15); 1.66/1.70 (1H, m, H-14); 1.90/1.94 (H-1, m, H-8); 2.57 & 2.68/2.29 & 2.86 (2H, m & m, H-20); 3.58 (3H, m, —O—CH$_3$); 3.62/3.87 (1H, m, H-21); 4.27 (2H, m, —O—CH$_2$—CH$_3$); 5.15 (1H, m, H-4); 5.27 (1H, m, H-6).
$^{13}$C NMR {125 MHz, CDCl$_3$(TMS), δ (ppm)[major/minor]}: 10.0/9.1 (CP (15β,16β)(CH$_2$)); 14.1 (—O—CH$_2$—CH$_3$); 16.7/17.1 (C-15); 18.88/18.16 (C-19); 19.7/20.1 (C-18); 24.6/23.6 (C-16); 30.77/30.85 (C-8); 34.9/33.9 (C-20); 47.4/47.5 (C-21); 48.6/48.7 (C-9); 52.31/53.1 (C-14); 54.312/54.303 (—O—CH$_3$); 62.12/62.07 (—O—CH$_2$—CH$_3$); 95.5 (95.7 (C-17); 98.5 (C-4); 117.5 (C-6); 141.2/141.34 (C-5); 155.46/155.50 (C-3); 168.05/168.06 (—CO—O—CH$_2$—CH$_3$); 171.5/171.3 (C-22).

EXAMPLE 6

17-Hydroxy-15β,16β-methylene-3-oxo-17α-pregna-4,6-diene-21,21-dicarboxylic acid ethyl ester γ-lactone 12 g (27.23 mmol) of 17-hydroxy-15β,16β-methylene-3-methoxy-17α-pregna-3,5-diene-21,21-dicarboxylic acid ethyl ester γ-lactone is dissolved in 300 μl of acetone under nitrogen atmosphere with vigorous stirring at room temperature, 36 ml of water and 7.2 g (29.28 mmol) of tetrachlorobenzoquinone are added and the reaction mixture is stirred for 4 hours, when the reaction is complete. The excess of the tetrachlorobenzoquinone is decomposed by addition of 16 g of sodium pyrosulfite dissolved in 200 ml of water and the mixture is stirred for 0.5 hour. The acetone solvent is removed by distillation under reduced pressure. To the residue 240 ml of dichloromethane is added, the precipitated "hydroquinone" is removed by filtration and washed by suspending it in 50 ml dichloromethane. Dichloromethane solutions are combined, extracted with 80 ml of 10% sodium hydroxide solution, washed with water to make it neutral, and then the dichloromethane is evaporated. To the residue 100-100 ml of methanol are added in two repetitions, which again, are removed by distillation. The residue is stirred with 30 ml of methanol for 30 minutes, the crystalline substance is washed twice with 10 ml of methanol cooled to 0° C. to remove the mother liquor and is dried in vacuo to constant weight at a temperature below 40° C., yielding 8.93 g (77.25%) of the title compound.

Mp: 158-161° C.
$[\alpha]_D^{25}=-17.0°$ (c=1%, chloroform)
The product contains 2 isomers in about 4:1 molar ratio.
$^1$H NMR {500 MHz, CDCl$_3$(TMS), δ (ppm) [major/minor]}: 0.60 & 1.35/0.56 & 1.34 (2H, m & m, CP (15β,16β)(CH$_2$)); 1.06/1.12 (3H, s, 18-Me); 1.13/1.14 (3H, s, 19-Me), 1.26 (1H, m, H-9); 1.32 (3H, t, —O—CH$_2$—C$_3$); 1.35/1.42

(1H, m, H-16); 1.58/1.56 (1H, m, H-15); 1.82/1.85 (1H, m, H-14); 2.44/2.50 (H-1, m, H-8); 2.63/2.29 & 2.86 (2H, m & m, H-20); 3.60/3.88 (1H, m, H-21); 4.27 (2H, m, —O—CH$_2$—CH$_3$); 5.71 (1H, m, H-4); 6.20 (1H, m, H-6); 6.34 (1H, m, H-7).

$^{13}$C NMR {125 MHz, CDCl$_3$ (TMS), δ (ppm)[major/minor]}: 10.4/9.5 (CP (15β,16β)(CH$_2$)); 14.11/14.12 (—O—CH$_2$—CH$_3$); 16.23/16.6 (C-15); 16.28/16.25 (C-19); 19.7/20.1 (C-18); 24.9/23.9 (C-16); 34.8/33.7 (C-20); 36.39/36.37 (C-8); 47.25/47.29 (C-21); 49.6/50.3 (C-14); 51.0/51.1 (C-9); 62.22/62.16 (—O—CH$_2$—CO$_3$); 94.8/94.9 (C-17); 124.18/124.13 (C-4); 128.66/128.64 (C-6); 139.4/139.7 (C-7); 162.9/163.1 (C-5); 167.82/167.86 (—CO—O—CH$_2$—CH$_3$); 171.2/171.0 (C-22); 199.2/199.3 (C-3).

EXAMPLE 7

17-Hydroxy-6ξ,7ξ;15β,16β-bismethylene-3-oxo-17α-pregna-4-ene-21,21-dicarboxylic acid ethyl ester γ-lactone (crude carbethoxy-drospirenone)

20 g (90.88 mol) of trimethylsulfoxonium iodide is dissolved in 400 ml of dimethyl sulfoxide in nitrogen atmosphere with vigorous stirring, then 5 g (89.28 mmol) of potassium hydroxide is added at 25-30° C. and the solution is stirred for 10 minutes. 8 g (18.84 mmol) of 17-hydroxy-15β,16β-methylene-3-oxo-17α-pregna-4,6-diene-21,21-dicarboxylic acid ethyl ester γ-lactone is added and the mixture is stirred for 24 hours at room temperature, then is slowly added to a mixture of water (4 l) and concentrated hydrochloric acid (10 ml). The precipitate formed, after 0.5 hour is filtered, washed with portions of water until it is neutral and dried in vacuo to constant weight at a temperature below 40° C. to yield 7.82 g (94.67%) of the title compound.

Mp: 125/135-140° C.

$[\alpha]_D^{25}$=−87.33°(c=0.5%, chloroform).

EXAMPLE 8

17-Hydroxy-6β,7β,15β,16β-bismethylene-3-oxo-17α-pregn-4-ene-21,21-dicarboxylic acid ethyl ester γ-lactone (carbethoxy-drospirenone)

3 g of crude carbethoxy-drospirenone is subjected to column chromatography; 68 g of silica gel Si60 (0.040-0.063 mm; manufacturer: Merck) and ethyl acetate/cyclohexane mixture of 55:45 volume ratio are used. Fractions having approximately the same composition and rich in carbethoxy-drospirenone are combined and the eluent is removed by distillation. The column is regenerated with acetone, conditioned with cyclohexane/acetone mixture of 3:1 volume ratio, then 2 g of the residue obtained above is chromatographed in 0.67 g portions (using the same eluent as above) by injecting said portions to the column at 90 minutes intervals. Fractions are monitored by TLC, those containing more than 95% of carbethoxy-drospirenone were combined, evaporated and from the residue ethanol was distilled off and finally the residue was crystallized from an ethanol/distilled water mixture of 30:70 volume ratio, yielding 0.76 g solid, containing more than 96% of carbethoxy-drospirenone (HPLC).

Mp: 106-108° C.

Since the ethoxycarbonyl group may exist in two different steric arrangements, the product contains two isomers at about 3:2 molar ratio.

$^1$H NMR {500 MHz, CDCl$_3$(TMS), δ (ppm)[major/minor]}: 0.58 & 1.36/0.54 & 1.33 (2H, m & m, CP (15β,16β)(CH$_2$)); 0.87 & 1.20 (2H, m & m, CP (6β,7β)(CH$_2$)); 0.98/1.04 (3H, s, 18-Me); 1.10/1.11 (3H, d, 19-Me); 1.12 (1H, m, H-9); 1.33 (3H, t, —O—CH$_2$—CH$_3$); 1.41/1.43 (1H, m, H-16); 1.49 (1H, m, H-7); 1.63/1.61 (1H, m, H-15); 1.64 (1H, m, H-6); 1.77/1.82 (1H, m, H-8); 1.94/1.97 (1H, m, H-14); 2.64/2.32 & 2.87 (2H, m & m, H-2); 3.60/3:89 (1H, m, H-21); 4.28 (2H, m & m, —O—CH$_2$—CH$_3$); 6.03 (1H, m, H-4).

$^{13}$C NMR {125 MHz, CDCl$_3$(TMS), δ (ppm)[major/minor]}: 10.4/90.5 (CP (15β,16β)(CH$_2$)); 14.11/14.12 (—O—CH$_2$—CH$_3$); 168/17.2 (C-15): 17.64/17.59 (C-19); 18.76/18.78 (CP (6β,7β)(CH$_2$)); 18.98/18.95 (C-6); 19.62/19.73 (C-7); 19.62/20.0 (C-18); 24.7/23.7 (C-16); 34.292/34.285 (C-8); 34.8/33.7 (C-20); 47.3/47.1 (C-21); 51.63/51.66 (C-9); 51.66/52.4 (C-14); 62.2/62.1 (—O—CH$_2$—CH$_3$); 95.0/95.1 (C-17); 125.91/125.90 (C-4); 167.88/167.92 (—CO—O—CH$_2$—CH$_3$); 170.9/171.03 (C-5); 171.2/171.64 (C-22); 197.7/197.8 (C-3).

Fractions with nearly the same quality and rich in 6α,7α-isomers are combined and evaporated. The residue is crystallized from ethanol/water 1:10 vol %.

$^1$H NMR {500 MHz CDCl$_3$(TMS, δ (ppm)[major/minor]}: 0.54 & 1.33/0.51 & 1.30 (2H, m & m, CP (15β,16β)(CH$_2$)); 0.56 & 0.94 (2H, m & m, CP (6α,7α)(CH$_2$)); 0.81 (1H, m, H-9); 1.05/4.11 (3H, s, 18-Me); 1.15/1.16 (3H, s, 19-Me); 1.32 (3H, t, —O—CH$_2$—CH$_3$); 1.39/1.37 (1H, m, H-16); 1.52 (1H, m, H-7); 1.58/1.56 (1H, m, H-15); 1.71/1.73 (1H, m, H-14); 1.82 (1H, m, H-6); 2.23/2.29 (1H, m, H-8); 2.63/2.31 & 2.84 (2H, m & m, H-20); 3.59/3.88 (1H, m, H-21); 4.27 (2H, m, —O—CH$_2$—CH$_3$); 5.96 (1H, m, H-4)

$^{13}$C NMR {125 MHz, CDCl$_3$(TMS), δ (ppm)[major/minor]}: 8.56/8.52 (CP (6α,7α)(CH$_2$)); 10.1/9.2 (CP (150,160)(CH$_2$)); 14.1 (—O—CH$_2$—CH$_3$); 14.5/14.6 (C-7); 15.7 (C-6); 16.5/16.9 (C-15): 17.1 (C-19); 19.9/20.4 (C-18); 24.6/23.6 (C-16); 30.4/30.3 (C-8); 34.9/33.7 (C-20); 41.93/41.89 (C-9); 47.28/47.34 (C-21); 50.4/51.1 (C-14); 62.18/62.12 (—O—CH$_2$—CH$_3$); 95.13/95.23 (C-17); 126.90/126.87 (C-4); 167.88/167.93 (—CO—O—CH$_2$—CH$_3$); 171.26/171.44 (C-5); 171.26/171.07 (C-22); 197.77/197.85 (C-3)

EXAMPLE 9

17-Hydroxy-6ξ,7ξ;15β,16β-bismethylene-3-oxo-17α-pregn-4-ene-21,21-carboxylic acid γ-lactone (crude drospirenone)

4.8 g (10.94=mol) of 17-hydroxy-6ξ,7ξ;15β,16β-bismethylene-3-oxo-17α-pregn-4-ene-21,21-dicarboxylic acid ethyl ester γ-lactone is dissolved in dimethylformamide (15 ml) under nitrogen atmosphere with vigorous stirring. To this solution 2 g of sodium chloride and 0.4 ml of water are added, the mixture is refluxed for 8 hours, then cooled to room temperature and diluted with 100 ml of water. The sticky product obtained is dissolved in 100 ml of dichloromethane, extracted with 15 ml of saturated sodium chloride and the dichloromethane is removed by distillation. From the residue the rest of the dimethylformamide is removed at 13.33 Pa (0.1 mmHg), then the residue is triturated with 100 ml of water, filtered, washed to remove the mother liquor and dried in vacuo to constant weight at a temperature below 40° C., yielding 3.2 g (79.8%) of the compound.

Mp: 96-130° C.

The product is a mixture of 6β,7β and 6α,7α isomers (ratio: 69:26)

EXAMPLE 10

17-Hydroxy-6β,7β;15β,16β-bismethylene-3-oxo-17α-pregn-4-ene-21-carboxylic acid γ-lactone 21.5 g of crude drospirenone prepared according to Example 9, is chromatographed by using 220 g of silica gel Si60 (0.040-0.063 mm; Merck) and ethyl acetate/cyclohexane mixture (1:1 volume ratio). Fractions are monitored by TLC, those having the same composition are combinated and the solvent is removed by distillation. To the residue cyclohexane is added dropwise, the precipitate (prechromatographed drospirenone) is filtered and dried in vacuo at a temperature below 40° C. 14.9 g of pre-chromatographed product is obtained containing 80% of drospirenone, which—after regeneration of the silica gel column with acetone and conditioning with cyclohexane/acetone (73:27 volume ratio)—is injected to the column in 2 g portions at 90 minutes intervals using cyclohexane/acetone eluent (volume ratio: 73:27).

Fractions of the same composition are combined, evaporated and the residue is crystallized from dichloromethane/diisopropyl ether mixture (10:90 vol %) to yield 9.7 g (45%) of pure drospirenone.

Mp: 199-201° C.

$^1$H NMR {500 MHz, CDCl$_3$(TMS), δ (ppm)}: 0.53 & 1.33 (2H, m & m, CP (15β,16β)(CH$_2$)); 0.87 & 1.22 (2H, m & m, CP (6β,7β)(CH$_2$)); 1.00 (3H, s, 18-Me); 1.10 (3H, d, 19-Me); 1.12 (1H, m, H-9); 1.36 (1H, m, H-16); 1.50 (1H, m, H-7); 1.59 (1H, m H-15); 1.64 (1H, m, H-6); 1.79 (1H, m, H-8); 1.95 (1H, m, H-14); 2.11 & 2.44 (2H, m & m, H-20); 2.53 & 2.64 (2H, m & m, H-21); 6.03 (1H, m, H-4).

$^{13}$C NMR {125 MHz, CDCl$_3$(TMS), δ (ppm)}: 10.0 (CP (15β,16β)(CH$_2$)); 16.6 (C-15) 17.6 (C-19); 18.8 (CP (6β,7β)(CH$_2$)); 19.0 (C-6); 19.73 (C-18); 19.75 (C-7); 24.6 (C-16); 29.3 (C-21); 30.7 (C-20); 34.3 (C-8); 51.7 (C-9); 51.9 (C-14); 96.1 (C-17); 125.9 (C-4); 171.1 (C-5); 176.5 (C-22); 197.8 (C-3).

EXAMPLE 11

17-Hydroxy-15β,16β-methylene-3-oxo-17α-pregna-4,6-diene-21-carboxylic acid γ-lactone 6.8 g (16.48 mmol) of 17-hydroxy-15β,16β-methylene-3-oxo-17α-pregna-4,6-diene-21,21-dicarboxylic acid ethyl ester γ-lactone is dissolved in dimethylformamide (20 ml) under nitrogen atmosphere with stirring. To the solution 1.4 g of sodium chloride and 0.45 ml water are added and the mixture is refluxed for 8 hours. The reaction mixture is cooled to 60° C. and 30 ml of water is added very slowly. The precipitate is filtered, washed with water to remove the mother liquor and dried to constant weight at 40° C., to give 4 g (71.27%) of the title compound.

Mp: 164-166° C.

$[α]_D^{25}$=36.6° (c=1%, chloroform).

$^1$H NMR {500 MHz CDCl$_3$ (7.27 ppm), δ (ppm)}: 0.54 & 1.30 (2H, m & m, CP (15β,16β)(CH$_2$)); 1.06 (3H, s, 18-Me); 1.12 (3H, s, 19-Me); 1.25 (1H, m, H-9); 1.35 (1H, m, H-16); 1.52 (1H, m, H-15); 1.81 (1H, m, H-14); 2.08 & 2.40 (2H, m & m, H-20); 2.44 (H-1H, m, H-8); 2.51 & 2.61 (2H, m & m, H-21); 5.68 (1H, m, H-4); 6.18 (1H, m, H-6); 6.34 (1H, m, H-7).

$^{13}$C NMR {125 MHz, CDCl$_3$ (77.03 ppm), δ (ppm)}: 9.9 (CP (15β,16β)(CH$_2$)); 16.0 (C-15); 16.2 (C-19); 19.7 (C-18); 24.5 (C-16); 29.2 (C-21); 30.6 (C-20); 36.3 (C-8); 49.7 (C-14); 51.0 (C-9); 95.9 (C-17); 124.0 (C-4); 128.5 (C-6); 139.7 (C-7); 163.1 (C-5); 176.4 (C-22); 199.2 (C-3).

EXAMPLE 12

17-Hydroxy-6ξ,7ξ;15β,16β-bismethylene-3-oxo-17α-pregn-4-ene-21-carboxylic acid γ-lactone (crude drospirenon)

60 g of trimethylsulfoxonium iodide is stirred in 1200 ml of dry dimethyl-sulfoxide under nitrogen atmosphere for 5-10 minutes, then 16 g of potassium hydroxide is added and stirring is continued for additional 1 hour. Dissolution of the potassium hydroxide is not complete. To this reagent 20 g of 17-hydroxy-15β,16β-methylene-3-oxo-17α-pregna-4,6-diene-21-carboxylic acid γ-lactone is added. Stirring is continued under nitrogen atmosphere (the heterogenous mixture become homogenous after 2-4 hours). The reaction is monitored by HPLC. After 20-24 hours the reaction mixture is slowly added to 10 l of water cooled to 10-12° C., said mixture is stirred until the precipitate is dense enough to filter, the crystals are washed with water to neutral and then dried in vacuo to constant weight at a temperature below 40° C.

Yield: 19 g (82.97%) crude drospirenone

The product is a mixture of 6β, 7β and 6α, 7α isomers (ratio: 68:25)

EXAMPLE 13

17-Hydroxy-6β,7β;15β,16β-bismethylene-3-oxo-17α-pregn-4-ene-21-carboxylic acid γ-lactone (drospirenone)

2 g (4.56 mmol) of 17-hydroxy-6β,7β;15β,16β-bismethylene-3-oxo-17α-pregn-4-ene-21,21-dicarboxylic acid ethyl ester γ-lactone is dissolved in 6 ml of dimethylformamide under nitrogen atmosphere with vigorous stirring. To this solution 0.8 g of sodium chloride and 0.15 ml of water are added and the solution is refluxed for 8 hours. The reaction mixture is cooled to room temperature, diluted with 40 ml of water. The sticky precipitate is dissolved in 40 ml dichloromethane, the solution is extracted with 6 ml of saturated aqueous sodium chloride solution. The dichloromethane is removed by distillation. From the residue the rest of the dimethylformamide is removed at 13.33 Pa (0.1 mmHg). The residue is triturated with 120 ml of water, filtered, washed to remove the mother liquor and dried in vacuo to constant weight at a temperature below 40° C. The dry product is recrystallized from acetone/disopropyl ether (10:90 vol %) to give 0.95 g (55.02%) of the title compound.

Mp: 199-201° C.

$^1$H NMR {500 MHz, CDCl$_3$(TMS), δ (ppm)}: 0.53 & 1.33 (2H, m & m, CP (15β,16β)(CH$_2$)); 0.87 & 1.22 (2H, m & m, CP (6β,7β)(CH$_2$)); 1.00 (3H, s, 18-Me); 1.10 (3H, d, 19-Me); 1.12 (1H, m, H-9); 1.36 (1H, m, H-16); 1.50 (1H, m, H-7); 1.59 (1H, m, H-15); 1.64 (1H, m, H-6); 1.79 (1H, m, H-8); 1.95 (1H, m, H-14); 2.11 & 2.44 (2H, m & m, H-20); 2.53 & 2.64 (2H, m & m, H-21); 6.03 (1H, m, H-4).

$^{13}$C NMR {125 MHz, CDCl$_3$(TMS) δ (ppm)}: 10.0 (CP (15β,16β)(CH$_2$)); 16.6 (C-15); 17.6 (C-19); 18.8 (CP (6β,7β) (CH$_2$)); 19.0 (C-6); 19.73 (C-18); 19.75 (C-7); 24.6 (C-16); 29.3 (C-21); 30.7 (C-20); 34.3 (C-8); 51.7 (C-9); 51.9 (C-14); 96.1 (C-17); 125.9 (C-4); 171.1 (C-5); 176.5 (C-22); 197.8 (C-3).

EXAMPLE 14

17-Hydroxy-6β,7β;15β,16β-bismethylene-3-oxo-17α-pregn-4-ene-21-carboxylic acid γ-lactone Pre-Purification with Cyclohexane/Ethyl Acetate/Aceton Eluent Mixture (Ratio: 64:18:18: Vol %)

A glass column (length, 46 cm, diameter: 2.6 cm) is packed with 120 g of silica gel (UETICON C-GEL, C-490, particle size: 15-35 pin) by the dry packing technique, wetted and conditioned with cyclohexane/ethyl acetate/acetone eluent mixture (64:18:18 vol %). 4 g of crude drospirenone is dissolved in 30 ml of ethyl acetate and the solution is loaded to column by using an eluent pump. Then the eluent is loaded to the column with a flow rate of 4.5 ml/min. In the process UV detection is applied. Fractions containing the target substance are analysed by TLC. Based on the TLC results fractions containing the drospirenone are combined into a so called "pre-purified" and into a "mixed" fraction. Said fractions are evaporated to dryness and the solid substances are crystallized from dichloromethane/diizopropyl ether (10:90 vol %). The "mixed" fraction contains—besides the target substance drospirenon—the 6α,7α-isomer in nearly such amount as it is present in the starting material (25-30%), while the "pre-purified" fraction contains the drospirenone besides maximum 2% of the 6α,7α-isomer. From the 4 g of drospirenone loaded approximatively 1.75 g "pre-purified" drospirenone is obtained. The "mixed" fraction gave 0.95 g of dry solid, which can be recirculated into the pre-chromatographic procedure.

Fine Purification by HPLC

A HPLC column (compacted package length: about 60 cm, diameter: 5 cm) is packed with 510 g of silica gel (UETICON C-GEL C-490, particle size: 15-35 μm) by slurry technique, then conditioned with cyclohexane/ethyl acetate/acetone eluent mixture (64:18:18 vol %). 5.1 g of pre-purified drospirenone (6α, 7α-isomer content max 2%) is dissolved in 80 ml of ethyl acetate and is injected to the column. Elution is carried out at 40 ml/min flow rate. The elute leaving the column is subjected to UV detection. From the detected break-through of the drospirenone to the end 80 ml fractions are collected which are qualified by HPLC. Based on the HPLC analysis fractions are combined into a "mixed" and a "fine chromatographed" fraction, said fractions are evaporated and crystallized from dichloromethane/diisopropyl ether mixture (10:90 v/v). The "mixed" crystal substance weighs 0.2-0.3 g and can be recirculated into the fine chromatographic process. The "fine chromatographed" fraction gave 4.4-4.5 g of drospirenon with a 6α,7α-isomer content below 0.1%. With repeated fine chromatography a product with the same purity is obtained.

The invention claimed is:

1. A process for the preparation of 17-hydroxy-6β,7β;15β,16β-bismethylene-3-oxo-17α-pregn-4-ene-21-carboxylic acid γ-lactone of the formula (I),

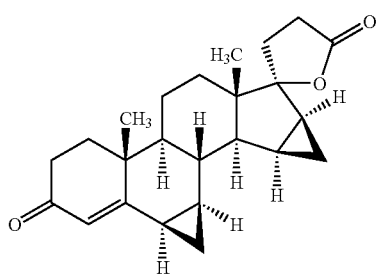

(I)

from 15α-hydroxy-androst-4-ene-3,17-dione of the formula (II)

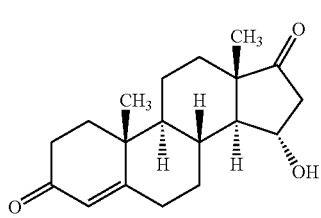

(II)

characterized in that
the 15α-hydroxy-androst-4-ene-3,17-dione of the formula (II)

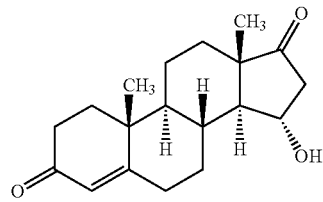

(II)

is acetylated with acetic anhydride in dry tetrahydrofuran in the presence of 4-dimethylaminopyridine catalyst at room temperature to give the 15α-acetoxyandrost-4-ene-13,17-dione of the formula (III),

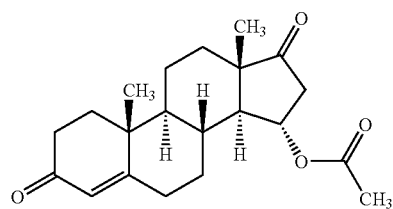

(III)

said compound of the formula (III) in dry tetrahydrofuran is reacted with a trialkoxy orthoformiate containing alkyl groups having from 1 to 5 carbon atoms, in the presence of sulfuric acid catalyst at 0-10° C. temperature to yield 15α-acetoxy-3-alkoxy-androsta-3,5-diene-17-one of the general formula (IV),

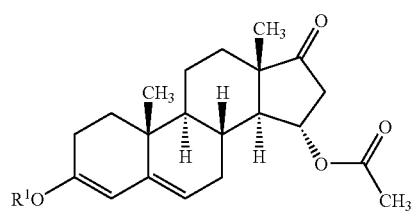

(IV)

wherein $R^1$ stands for an alkyl group having 1-4 carbon atoms,
said compound of the general formula (IV) is reacted with a trimethylsulfoxonium methylide in situ prepared in dimethyl sulfoxide from a trimethylsulfoxonium salt with an alkali metal hydroxide, to give the 15β,16β-methylene-3-alkoxy-androsta-3,5-diene-17-one of the general formula (V),

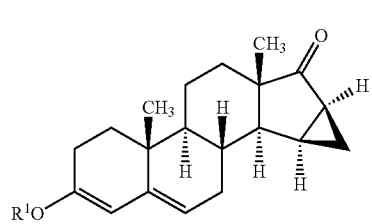

(V)

said compound of the general formula (V)—wherein $R^1$ stands for an alkyl group having 1-4 carbon atoms—in dimethyl sulfoxide is reacted with trimethysulfonium iodide in the presence of potassium tert-butylate at a temperature of 15-25° C. to give the 15β,16β-methylene-3-alkoxy-spiro[androsta-3,5-diene-17β2'-oxirane] of the general formula (VI),

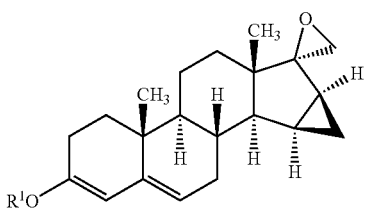
(VI)

wherein $R^1$ stands for an alkyl group having 1-4 carbon atoms,
said compound of the of the general formula (VI) in ethanol is reacted with a di (C$_{1-4}$ alkyl)malonate in the presence of sodium ethoxide under boiling to yield 17-hydroxy-15β,16β-methylene-3-alkoxy-17α-pregna-3,5-diene-21,21-dicarboxylic acid alkyl ester γ-lactone of the general formula (VII),

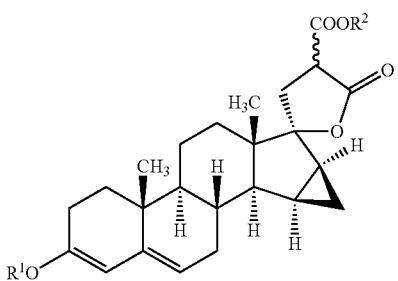
(VII)

wherein $R^1$ and $R^2$ stand for an alkyl group having 1-4 carbon atoms, and the ~ bond represents α and β configuration,
said compound of the general formula (VII) is dehydrogenated with tetrachlorobenzoquinone in acetone to give 17-hydroxy-15β,16β-methylene-3-oxo-17α-pregna-4,6-diene-21,21-dicarboxylic acid alkyl ester γ-lactone of the general formula (VIII),

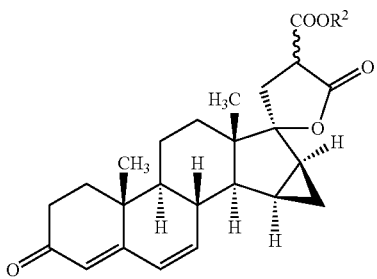
(VIII)

wherein $R^2$ stands for an alkyl group having 1-4 carbon atoms and the ~ bond represents α and β configuration,
said compound of the formula (VIII) is reacted with trimethylsulfoxonium methylide in situ prepared in dimethyl sulfoxide from a trimethylsulfoxonium salt and an alkali metal hydroxide to give 17-hydroxy-6ξ,7ξ;15β,16β-bismethylene-3-oxo-17α-pregn-4-ene-21,21-dicarboxylic acid alkyl ester γ-lactone of the general formula (IX),

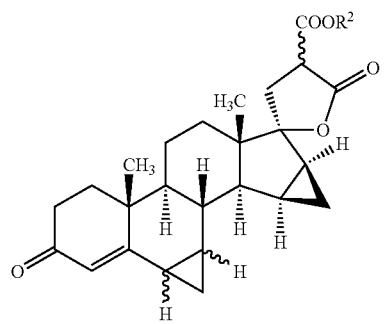
(IX)

wherein $R^2$ is an alkyl group having 1-4 carbon atoms and the ~ bond represents α and β configuration,
and either from said compound of the general formula (IX) the 17-hydroxy-6β,7β;15β,16β-bismethylene-3-oxo-17α-pregn-4-ene-21,21-dicarboxylic acid alkyl ester γ-lactone (an isomer of the general formula (IXa)) is isolated by chromatography and recrystallization—in general formula (IXa) $R^2$ and the ~ bond are as defined above—

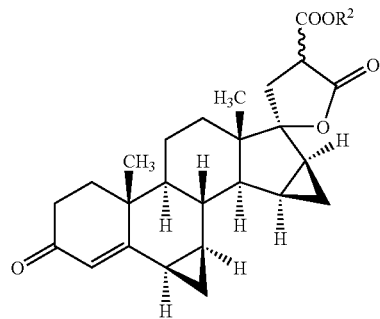
(IXa)

and said isomer of the general formula (IXa) in dimethylformamide is decarboxylated at a temperature around the boiling point of the reaction mixture to give the 17-hydroxy-6β,7β;15β;16β-bismethylene-3-oxo-17α-pregn-4-ene-21-carboxylic acid γ-lactone of the formula (I) which is isolated,
or the 17-hydroxy-6ξ,7ξ;15β,16β-bismethylene-3-oxo-17α-pregn-4-ene-21,21-dicarboxylic acid alkylester γ-lactone of the general formula (IX),

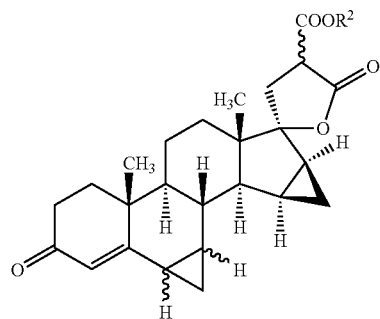
(IX)

wherein $R^2$ stands for an alkyl group having 1-4 carbon atoms and the ~ bond represents α and β configuration, in dimethylformamide is decarboxylated at a temperature around the boiling point of the reaction mixture to give 17-hydroxy-6ξ,7ξ;15β,16β-bismethylene-3-oxo-17α-pregn-4-ene-21-carboxylic acid γ-lactone of the formula (X),

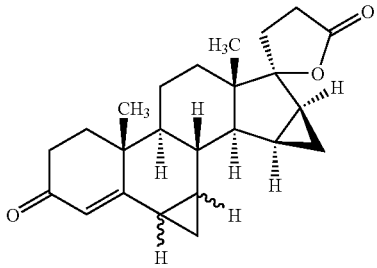
(X)

wherein the ~ bond represents α and β configuration, from which the 17-hydroxy-6β,7β;15β,16β-bismethylene-3-oxo-17α-pregn-4-ene-21-carboxylic acid γ-lactone of the formula (I) is separated by chromatography and recrystallization;
or
the 17-hydroxy-15β,16β-methylene-3-oxo-17α-pregna-4,6-diene-21,21-dicarboxylic acid alkyl ester γ-lactone of the general formula (VIII)

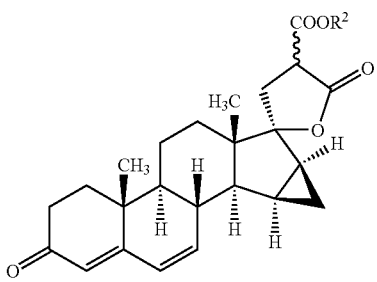
(VIII)

wherein R² stands for an alkyl group having 1-4 carbon atoms and the ~ bond represents α and β configuration, in dimethylformamide is decarboxylated at a temperature around the boiling point of the reaction mixture, to give the 17-hydroxy-15β,16β-methylene-3-oxo-17α-pregna-4,6-diene-21-carboxylic acid γ-lactone of the formula (VIIIa) which is isolated,

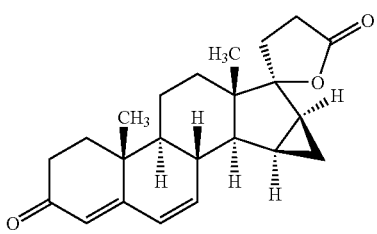
(VIIIa)

said compound of the formula (VIIIa) is reacted with trimethylsulfoxonium methylide prepared in situ in dimethyl sulfoxide from a trimethylsulfoxonium salt and an alkali metal hydroxide to yield 17-hydroxy-6ξ;7ξ;15β,16β-bismethylene-3-oxo-17α-pregn-4-ene-21-carboxylic acid γ-lactone of the formula (X),

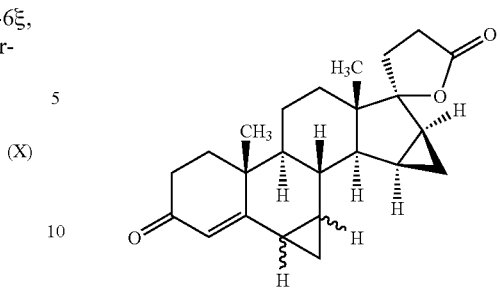
(X)

wherein the ~ bond represents α and β configuration, and from said compound of the formula (X) the 17-hydroxy-6ξ,7ξ;15β,16β-bismethylene-3-oxo-17α-pregn-4-ene-21carboxylic acid γ-lactone of the formula (I) is separated by chromatography and recrystallization.

2. A process according to claim 1, characterized in that the chromatographic separation of the isomeric products of the formula (X)—wherein the ~ bond represents α and β configuration—is carried out on silica gel.

3. A process according to claim 1, characterized in that the chromatographic separation of the isomeric products of the formula (X)—wherein the ~ bond represents α and β configuration—is carried out on silica gel in two stages using a preliminary and a fine chromatographic step.

4. A process according to claim 1, characterized in that the chromatographic separation of the isomeric products of the formula (X)—wherein the ~ bond represents α and β configuration—is carried out by using a cyclohexane/ethyl acetate/acetone mixture composed of 64:18:18 vol % of the components, or a cyclohexane/ethyl acetate/acetonitrile mixture composed of 55:35:10 vol % of the components, or a cyclohexane/methyl tert-butyl ether/acetone mixture composed of 50:30:20 vol % of the components or a cyclohexane/acetone mixture composed of 73:27 vol % of the components as eluent.

5. A process according to claim 1, characterized in that drospirenone of the formula (I) obtained in the process is crystallized from methanol, ethanol, propanol, isopropanol, ethyl acetate, aqueous mixtures containing up to 10 vol % of water selected from methanol/water, ethanol/water, propanol/water, isopropanol/water or an acetone/diisopropyl ether mixture containing up to 50 vol % of acetone, cyclohexane/ethyl acetate mixture containing up to 50 vol % of ethyl acetate, dichloromethane/diisopropyl ether mixture containing up to 10 vol % of dichloromethane, or dichloromethane/hexane mixture containing up to 10 vol % of dichloromethane.

6. A process according to claim 1, characterized in that the chromatography of the 17-hydroxy-6ξ,7ξ;15β,16β-bismethylene-3-oxo-17α-pregn-4-ene-21,21-dicarboxylic acid alkyl ester γ-lactone isomers of the general formula (IX)—wherein R² stands for an alkyl group having 1-4 carbon atoms, and the ~ bond represents α and β configuration—is carried out with an ethyl acetate/cyclohexane mixture composed of 55:45 vol % of the components.

7. The method of claim 1 wherein said compound of the formula (VIII) is reacted with trimethylsulfoxonium methylide in situ prepared in dimethyl sulfoxide from a trimethylsulfoxonium salt and an alkali metal hydroxide to give 17-hydroxy-6ξ,7ξ;15β,16β-bismethylene-3-oxo-17α-pregn-4-ene-21,21-dicarboxylic acid alkyl ester γ-lactone of the general formula (IX),

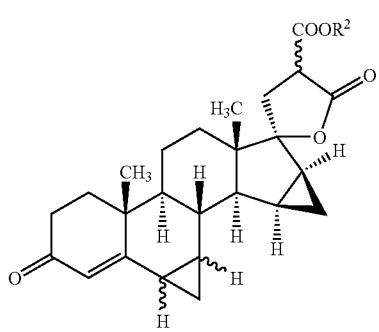

(IX)

wherein R² is an alkyl group having 1-4 carbon atoms and the ~ bond represents α and β configuration, and either from said compound of the general formula (IX) the 17-hydroxy-6β,7β;15β,16β-bismethylene-3-oxo-17α-pregn-4-ene-21,21-dicarboxylic acid alkyl ester γ-lactone (an isomer of the general formula (IXa)) is isolated by chromatography and recrystallization—in general formula (IXa) R² and the ~ bond are as defined above—

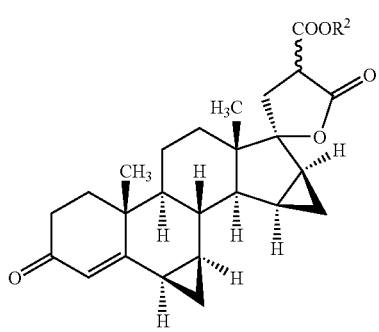

(IXa)

and said isomer of the general formula (IXa) in dimethylformamide is decarboxylated at a temperature around the boiling point of the reaction mixture to give the 17-hydroxy-6β,7β;15β;16β-bismethylene-3-oxo-17α-pregn-4-ene-21-carboxylic acid γ-lactone of the formula (I) which is isolated, or the 17-hydroxy-6ξ,7ξ;15β,16β-bismethylene-3-oxo-17α-pregn-4-ene-21,21-dicarboxylic acid alkylester γ-lactone of the general formula (IX),

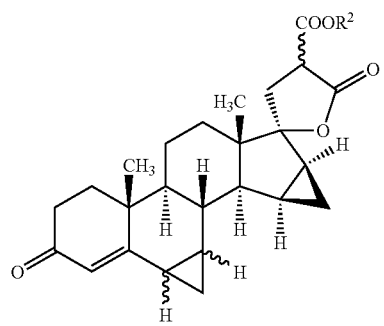

(IX)

wherein R² stands for an alkyl group having 1-4 carbon atoms and the ~ bond represents α and β configuration, in dimethylformamide is decarboxylated at a temperature around the boiling point of the reaction mixture to give 17-hydroxy-6ξ, 7ξ;15β,16β-bismethylene-3-oxo-17α-pregn-4-ene-21-carboxylic acid γ-lactone of the formula (X),

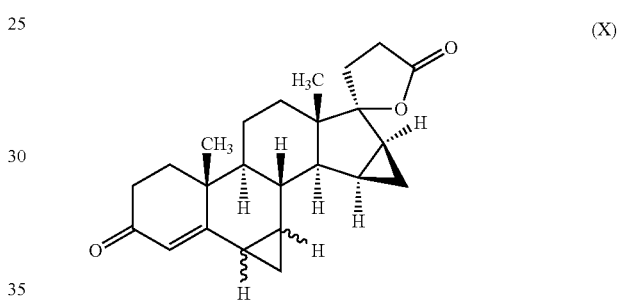

(X)

wherein the ~ bond represents α and β configuration, from which the 17-hydroxy-6β,7β;15β,16β-bismethylene-3-oxo-17α-pregn-4-ene-21-carboxylic acid γ-lactone of the formula (I) is separated by chromatography and recrystallization.

8. A process according to claim 1, wherein the compound of the general formula (VI) is purified in methanol.

9. A process according to claim 1, wherein the compound of the formula (IV) is crystallized from acetonitrile.

10. A process according to claim 1, wherein R¹ is methyl.

\* \* \* \* \*

UNITED STATES PATENT AND TRADEMARK OFFICE
CERTIFICATE OF CORRECTION

PATENT NO. : 8,450,476 B2
APPLICATION NO. : 11/719463
DATED : May 28, 2013
INVENTOR(S) : Gálik et al.

It is certified that error appears in the above-identified patent and that said Letters Patent is hereby corrected as shown below:

In the Claims:

At column 24, in Claim 1, lines 15-17, "17-hydroxy-6ξ,7ξ;15β.16β-bismethylene-3-oxo-17α-pregn-4-ene-21carboxylic" should read --17-hydroxy-6β,7β:15β,16β-bismethylene-3-oxo-17α-pregn-4-ene-21-carboxylic--.

Signed and Sealed this
Ninth Day of July, 2013

Teresa Stanek Rea
*Acting Director of the United States Patent and Trademark Office*